(12) United States Patent
Khaw

(10) Patent No.: US 7,942,804 B2
(45) Date of Patent: May 17, 2011

(54) REPLACEABLE EXPANDABLE TRANSMYOCARDIAL VENTRICULAR ASSIST DEVICE

(75) Inventor: Kenneth Khaw, Plainsboro, NJ (US)

(73) Assignee: Cor-Med Vascular, Inc., Plainsboro, NJ (US)

( * ) Notice: Subject to any disclaimer, the term of this patent is extended or adjusted under 35 U.S.C. 154(b) by 1752 days.

(21) Appl. No.: 11/134,226

(22) Filed: May 20, 2005

(65) Prior Publication Data

US 2006/0008349 A1 Jan. 12, 2006

Related U.S. Application Data

(60) Provisional application No. 60/572,390, filed on May 20, 2004.

(51) Int. Cl.
*A61M 1/12* (2006.01)
(52) U.S. Cl. .......................................................... 600/16
(58) Field of Classification Search .................... 600/16
See application file for complete search history.

(56) References Cited

U.S. PATENT DOCUMENTS

| | | | | |
|---|---|---|---|---|
| 4,143,661 A | * | 3/1979 | LaForge et al. | 607/61 |
| 5,163,910 A | * | 11/1992 | Schwartz et al. | 604/151 |
| 5,749,855 A | * | 5/1998 | Reitan | 604/151 |

OTHER PUBLICATIONS

Gillum, Richard F., Epidemiology of Heart Failure in the United States, Am Heart J 1993, 126:1042-1047.

* cited by examiner

*Primary Examiner* — Michael Kahelin
(74) *Attorney, Agent, or Firm* — Perkins Coie LLP; Patrick Morris

(57) ABSTRACT

A novel ventricular assist device is disclosed comprising a pump unit and a motor unit. The pump unit is made up of an impeller, an impeller housing, and a shaft. The impeller and/or the impeller housing are expandable, allowing for custom fitting and positioning of the pump unit within the ventricle. In certain embodiments, the shaft is adjustable, allowing for further customization of fit.

11 Claims, 4 Drawing Sheets

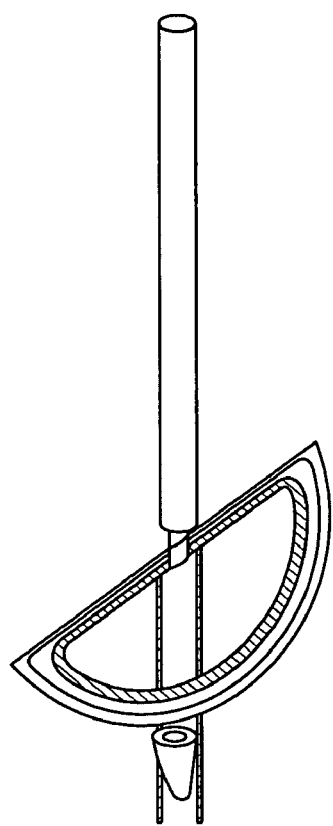
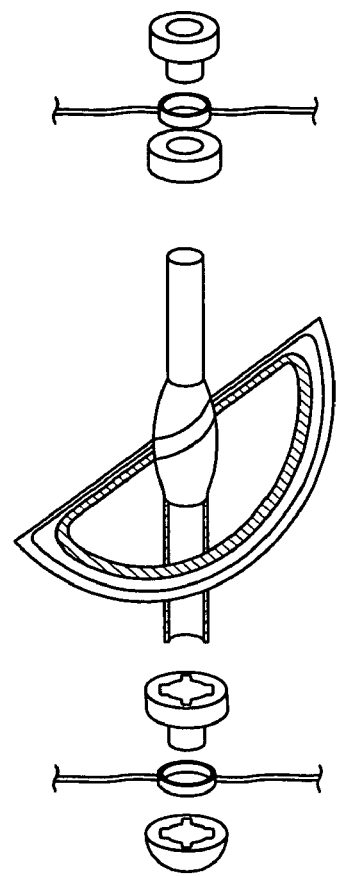
FIG. 3A
FIG. 3B
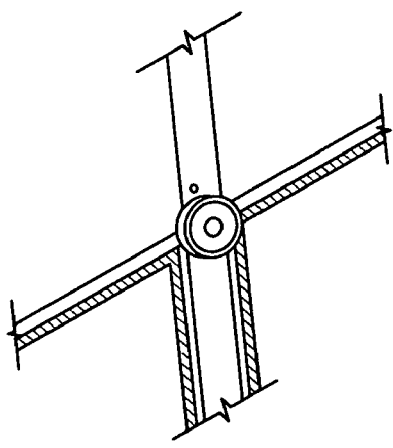
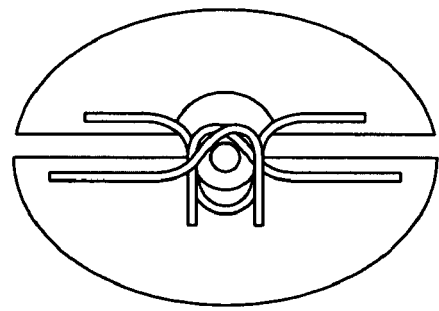
FIG. 3C
FIG. 3D

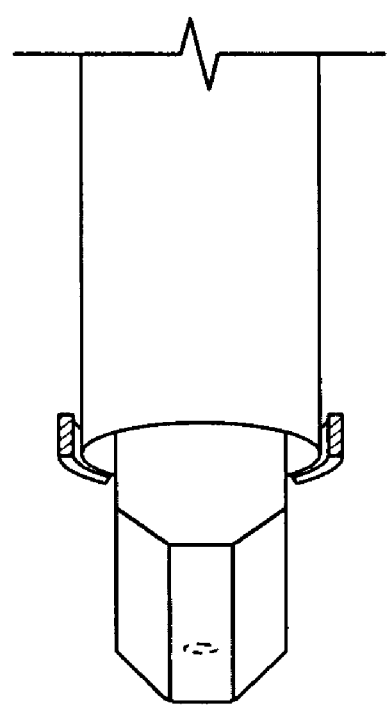 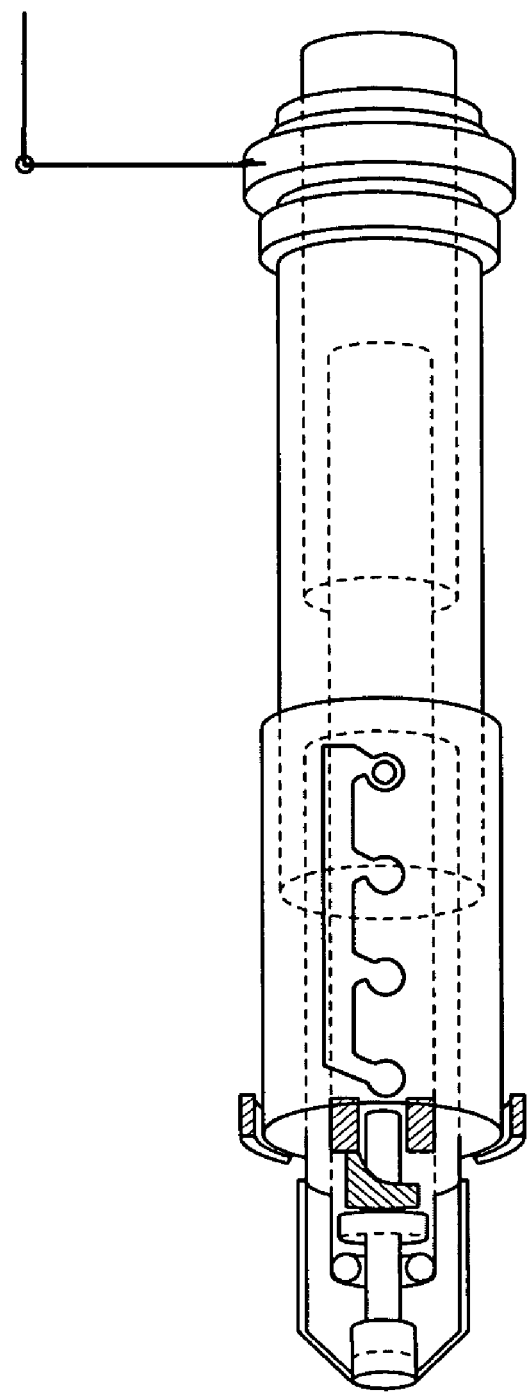
FIG. 4A  FIG. 4B

REPLACEABLE EXPANDABLE TRANSMYOCARDIAL VENTRICULAR ASSIST DEVICE

CROSS-REFERENCE TO RELATED APPLICATION

This application claims priority to U.S. Provisional Patent Application Ser. No. 60/572,390, filed May 20, 2004, the disclosure of which is incorporated by reference herein in its entirety, including drawings.

BACKGROUND

Congestive heart failure, characterized by an inability of the heart to pump a sufficient amount of blood, is a major worldwide health concern. In the United States alone, approximately 400,000 new cases are diagnosed annually (Gilum 1993). Congestive heart failure may arise from a variety of causes, including heart attacks, long-term high blood pressure, disease of the heart valves, or congenital heart defects. Patients with congestive heart failure are potential candidates for heart transplants, but there are not enough transplantable hearts available to satisfy the needs of each of these candidates.

A ventricular assist device (VAD) is a mechanical pump used to assist the heart in pumping blood through the body. VADs were originally designed for short-term use only, as a means to keep a patient alive until a heart transplant was available. However, in recent years VADs have begun to be used as a long-term therapy option for patients who are not heart transplant candidates. VADs partially relieve symptoms of severe heart failure such as shortness of breath and fatigue.

SUMMARY

An improved ventricular assist device is provided herein. In certain embodiments, the device is made up of a pump unit, which includes an expandable impeller, an expandable impeller housing, and a shaft, and a motor unit, which comprises a motor and a motor housing unit. In certain embodiments, the motor unit further comprises a power supply. The power supply may be external or internal, and may consist of one or more rechargeable batteries. In certain embodiments, the shaft is made up of two or more overlapping shafts, and the overall length of the shaft may be adjusted by altering the position of the overlapping shafts relative to one another.

BRIEF DESCRIPTION OF THE DRAWINGS

FIG. 3 shows an inflatable tubular frame for an impeller incorporated into an impeller shaft.

FIG. 4 shows a fixed impeller shaft (A) and an adjustable outer impeller shaft (B). The adjustable outer impeller shaft has a slotted channel and locks. The inner rotating shaft has a fixed length longer than the outer shaft. The inner rotating shaft can freely slide along the motor's shaft. The impeller shaft has separation points with smaller tubing to allow needle valve.

DETAILED DESCRIPTION

Figure 1:
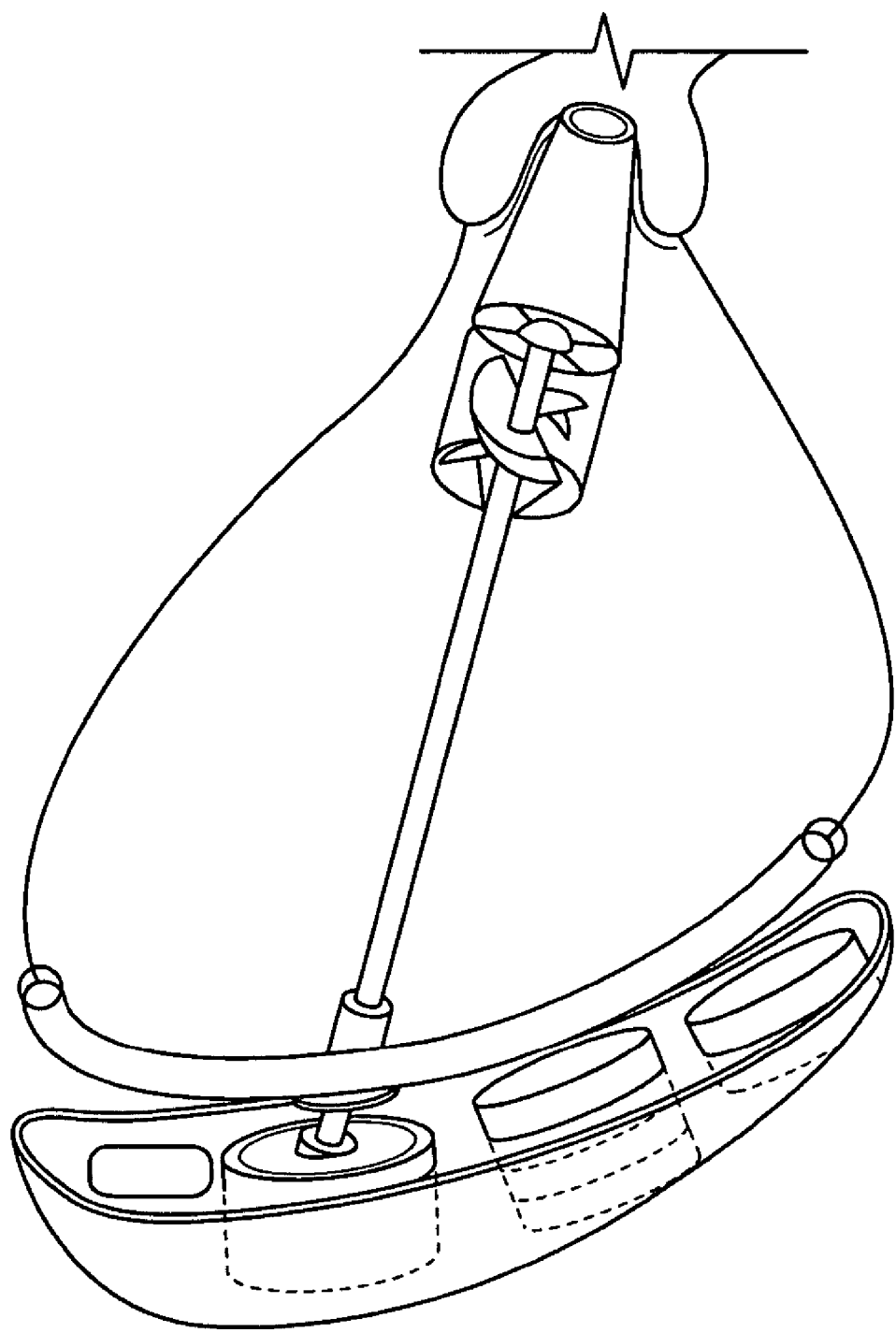
FIG. 1 shows an embodiment of a ventricular assist device.
Figure 2A:
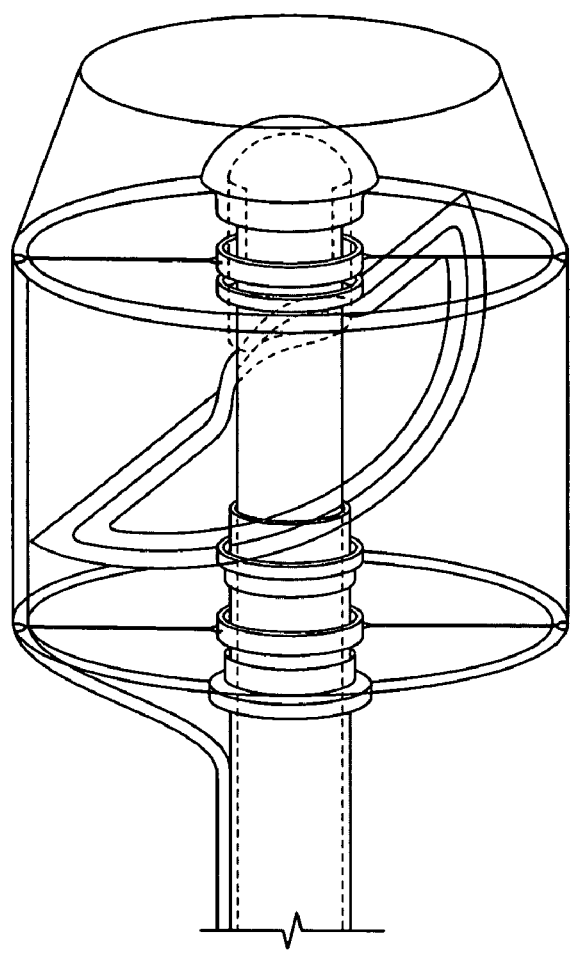
FIG. 2 shows an embodiment of an expandable impeller housing with a tapered tubular membrane extension and an expandable impeller. The membrane extension prevents the housing from prolapsing into the impeller. Inset A illustrates the path of the inflating tube within the housing. Inset B shows an embodiment of an expandable impeller housing in which the housing is made up of wire mesh.
Figure 2B:
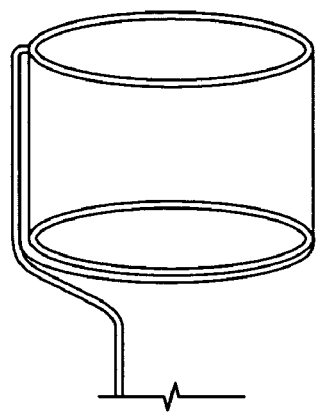
Figure 2C:
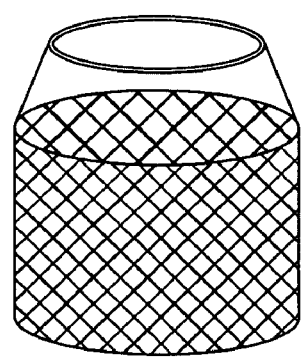

Ventricular assist devices (VADs) generally consist of a pump unit, a control system, and a power supply. Some VADs rely on a battery for their power supply, while others use a pneumatic system. Each of the components of the VAD may be located either inside or outside the body. Blood flows from the ventricles into the pump, where it is then expelled from the heart. A left ventricular assist device (LVAD) receives blood from the left ventricle and delivers it to the aorta, while a right ventricular assist device (RVAD) receives blood from the right ventricle and delivers it to the pulmonary artery. LVADs may be pulsatile, non-pulsatile, synchronous, or non-synchronous to the pumping of the natural heart. Types of LVADs include the axial pump, sac, diaphragm, pusher-plate, and centrifugal types.

The VAD disclosed herein can be used for temporary as well as destination therapy with video assisted thoracic surgery or traditional open heart surgery. It has the potential to pump up to 16 liters/minute from either ventricle, and includes safety features to prevent negative consequences arising from battery or motor failure. Since the device is made of plastic polymers and/or metal, surgeons can replace the device with video assisted technique or with a small incision in to the chest.

Pump Unit

The VAD disclosed herein utilizes an expandable pump unit to allow for custom fitting and positioning of the VAD. The pump unit comprises an impeller, an impeller housing, and a shaft. The impeller and the impeller housing may be expandable or inflatable, providing for ease of insertion into the ventricle and customized fitting. In addition, the shaft may be adjustable, allowing for alterations in length that further enhance customized fitting. The device is easily implantable and exchangeable, and may be implanted in either a temporary or a permanent manner. The VAD may be used on patients ranging in age from adulthood to neonatal stage.

The impeller is made up of a set of two or more blades. One skilled in the art will recognize that the size, number, and shape of the blades making up the impeller may be varied to optimize efficiency. In certain embodiments, the impeller may have from two to four blades. The impeller is designed to be expandable. In certain embodiments, the impeller is flexible, and expansion occurs when the impeller moves from a contracted state to a relaxed state. In other embodiments, expansion of the impeller is accomplished by inflating. In its unexpanded or uninflated state, the impeller may be collapsible or foldable. In its expanded or inflated state, the impeller blades derive their structural stiffness from one or more inflatable tubes, flexible metals, or a combination thereof. The inflatable tubes may be inflated using gas or liquid. The flexible metal may be a memory metal, such as for example nitinol. The surface of the impeller blades may be formed from any suitable material. For example, the surface may comprise one or more thin plastic membranes. In certain embodiments, an inflatable tube or metal wire providing structural stiffness to an impeller blade is sandwiched between two plastic membranes. In certain other embodiments, the edge of the impeller blade is folded or wrapped around the tube or wire. Molded nubs may be present on one or both sides of the attachment between the impeller and the shaft to dampen vibration and provide extra support for the impeller.

The impeller housing comprises one or more membranes, and forms a generally circular tubular structure in its expanded state. In certain embodiments, the impeller housing is flexible, and its expanded state occurs when it moves from a contracted state to a relaxed state. In other embodiments, expansion of the impeller housing is accomplished by inflation. In its expanded state, the impeller housing may derive structural support for its circular structure from one or more inflatable tubes, one or more flexible wires or rings, or a combination thereof. The flexible wires or rings may be made of a memory metal such as nitinol. In embodiments wherein the impeller housing derives support from inflatable tubes, the inflatable tubes are connected to a rigid tube near the impeller housing, with the inflating end having a needle valve. The inflatable tubes may be inflated with gas or liquid. In embodiments wherein the impeller housing derives support from flexible wires or rings, the wires or rings are self-expanding. The distal end of the impeller housing has a membrane extension, which is an extension of the membrane(s) making up the sides of the impeller housing. This membrane extension is longer than the diameter of the housing, and tapers to about one-third the diameter of the housing. On one side of the impeller housing there is a thin bent metal rod that extends from the impeller housing to the distal edge and back. This rod serves as a support to prevent the membrane from prolapsing back into the impeller.

The shaft of the pump unit is attached at or near one of its ends to the impeller housing in such a way that the end of the shaft lies inside the impeller housing. The shaft is thin, with a diameter ranging from about 0.25 to about 2.5 mm. In one embodiment, the shaft extends across the entire length of the impeller housing, with the end of the shaft contacting the membrane extension of the impeller housing. The shaft may be adjustable in length, allowing for custom fitting and positioning of the pump unit. This is useful due to variations in heart size, particularly variations associated with various stages of congestive heart failure. In other embodiments, the shaft may be solid, meaning that it has a fixed length. In certain embodiments, the shaft comprises one or more overlapping tubular shafts. One such embodiment is shown in represented in FIG. 4. FIG. 4*a* illustrates a fixed-length shaft comprising an inner impeller shaft and an outer housing shaft. FIG. 4*b* illustrates an adjustable shaft comprising an innermost impeller shaft, a middle housing shaft, and an outermost extender housing shaft. In embodiments wherein the shaft comprises one or more overlapping shafts, the position of the outermost shaft with respect to the inner shaft(s) may be adjusted, resulting in a change in overall shaft length. In these embodiments, the outermost shaft and/or the shaft adjacent to the outermost shaft may comprise one or more slots and/or notches for adjustment of the shaft length. The length of the shaft may be locked using one or more locking mechanisms. For example, one or more locking devices, such as a locking ring, may be present at one or both ends of the shaft. In other embodiments, adjacent shafts may comprise screw threads, slotted channels, complementary interlocking shapes, or the like, which allow the position of the shafts to be locked. In certain embodiments, one or more of the shafts in a multiple shaft structure may serve to lock the various shafts together and prevent slippage. For example, the diameter of one or more of the inner shafts may be increased such that it is no longer free to slide within the outer shaft. Likewise, the diameter of an outer shaft may be decreased, such that the inner shaft(s) is no longer free to slide within it. In addition, the shaft may incorporate one or more retainer rings or freely rotating rings.

In embodiments in which one or more components of the pump unit are inflatable, the pump unit further comprises an inflation tube for inflating and deflating the impeller and/or the impeller housing. The inflation tube may be located inside the shaft, or it may run adjacent to and outside of the shaft. In those embodiments wherein the shaft comprises multiple overlapping shafts, the inflation tube may be located inside the innermost shaft, between any two overlapping shafts, or outside of the outermost shaft.

In certain embodiments, one end of the inflation tube is sealed at the shaft, while the other attaches to a rigid plastic or metal tube after the bend at the shaft. The rigid tube runs towards the distal end of the main impeller shaft and has a slight overhang. Molded plastic inserts and mount rings for the impeller housing may go over these tubes and shaft to be glued and/or bonded. The end of the shaft and these small tubes will be capped. The small overhang allows direct connection to the shaft and prevents the adhesive or bonding from entering the inflation tube. The cap will have spacers and guides for the small rigid tube and main lumen for support.

In certain embodiments, the inflation port will have a needle valve that will be bonded to the impeller shaft. It will have a screw on cap to prevent leakage of the inflating fluid in case the valve fails. The volume in the cap when closed will have very little open space, preventing the inflated tube from depressurizing when the valve fails.

The metal rim may be made up of solid or braided metal. In embodiments in which it is solid metal, it may be a nickel titanium compound that does not deform as easily as stainless steel, such as nitinol. In embodiments in which the rim is made of braided metal, the braided metal may be stainless steel cable or other braided metals. The attachment to the shaft will be a hinge. There will be molded nubs on each side of the blade. The nub on the side of the motor will be able to slide forward and lock onto the shaft and sandwich the impeller blade. This will prevent vibration and hold the impeller blades in place. The end of the impeller shaft will have mounts for the impeller housing.

The impeller and the impeller housing are attached to one another via metal wires. In certain embodiments, the entire impeller/impeller housing unit can be collapsed and placed into a sheath, meaning that it may be deployed into the ventricle by a catheter. This sheath may be removed after the unit is placed inside the ventricle, at which point it can be removed and the unit can be expanded.

At the end opposite the impeller housing, the shaft is attached to motor housing base, which is in turn attached to the heart wall via suturing. In embodiments wherein the shaft comprises multiple overlapping shafts, the outermost shaft mates with the base via slots having shapes that prevent its rotation. Adjacent shafts may comprise screw threads that allow them to be tightened together. The direction of these threads is such that the outermost of the two shafts will tighten onto the innermost of the two shafts. A plastic or metal tube or rod can be cut to desired length and placed into the shaft to act as a stopper.

Motor Unit

In one embodiment, the motor housing comes in two parts, a base and a cap, which snap together in a claim shell manner to form a watertight seal. The motor housing contains a motor, and in certain embodiments may also contain a power source such as one or more rechargeable batteries. In addition, it may house electronics for battery charging and monitoring devices, one or more electronic control systems, and wire coils for receiving radio frequency or magnetic field energy. A base plate is used to anchor the motor housing to the heart wall. Following expansion, the pump unit is attached to this base. The motor has a generally flattened designed with a large shaft. It has a non-circular insert such as a hexagonal or square hollow insert, which allows the shaft to slide freely inside it while the motor is running.

In certain embodiments wherein the motor unit comprises a power supply, the power supply may be recharged using energy from a radio frequency or a magnetic field. For example, external radio frequency waves or magnetic fields may be generated by transmitting wire coils placed over the heart area of a patient. In some embodiments, these wire coils are contained within a wearable device, such as a vest. This wearable device may come in a variety of shapes and designs. Preferably, the wearable device is oriented such that the transmitting wire coils are close to the motor unit when the device is worn by a patient. The coils may be located at the front, back, or side of the patient, so long as they are in close enough proximity to transmit their energy to the receiving coils. Both the receiver and the transmitter will preferably be run by rechargeable batteries, such as lithium, nickel cadmium, or nickel metal hydride batteries. In certain embodiments, the wearable device batteries may be charged using external power source such as an AC outlet.

Implantation

In certain embodiments, the motor drive base, which has a curvature similar to the heart wall, is placed longitudinal to the heart axis, with the hole for the shaft near the apex. The base plate is first sutured onto the heart muscle wall and around the shaft. Access to the ventricle may be gained using a button hemostatic valve sheath. Modified Seldinger technique is used to get the guide wire across the aortic valve. A needle is placed in the ventricle, and a flexible wire is placed into the needle. The needle is then removed, and the wire is used as a guide for the button sheath with an obturator in it to push through the myocardium. The obturator is then removed and the button sheath is left to be sutured to the heart muscle. The pump unit can then be inserted through the sheath. A hemostatic valve will prevent blood from leaking out. In embodiments wherein the shaft comprises two or more overlapping shafts, the valve will have a slot or geometric surface, such as a hexagonal shape insert, that is continuous with the base and that will mate with the shaft. This will prevent rotation of the outermost shaft, while allowing the innermost shaft to rotate. The sheath is pulled back, the housing and impeller is expanded into place, and the impeller is locked. The shaft is snapped onto the base, and the remainder of the motor unit is attached to the base.

References

1. Gilum, R. F. 1993. Epidemiology of Heart Failure in the U.S. 126 Am Heart J 126:1042.

What is claimed is:

1. A ventricular assist device comprising:
   a) a pump unit comprising:
      i) an expandable impeller having inflatable blades;
      ii) an expandable impeller housing; and
      iii) a shaft; and
   b) an implantable motor unit that is adapted to be anchored to a heart wall comprising a motor contained within a motor housing, the motor housing having a curvature similar to the heart wall;
   wherein the expandable impeller and expandable impeller housing is adapted to be placed inside a left or right ventricle.

2. The ventricular assist device of claim 1, wherein the inflatable blades are inflated by gas or liquid.

3. The ventricular assist device of claim 1, wherein the expandable impeller housing, when expanded, forms a tubular shape.

4. The ventricular assist device of claim 3, wherein the expandable impeller housing derives its structural support from one or more inflatable tubes.

5. The ventricular assist device of claim 4, wherein the one or more inflatable tubes are inflated by gas or liquid.

6. The ventricular assist device of claim 3, wherein the expandable impeller housing derives its structural support from one or more self-expanding flexible wires or rings.

7. The ventricular assist device of claim 1, wherein the motor unit is adapted to be anchored to the heart wall via a base plate that is adapted to be sutured to a heart muscle of the heart wall.

8. The ventricular assist device of claim 1, wherein the motor housing contains a power source.

9. The ventricular assist device of claim 8, wherein the power source is one or more rechargeable batteries.

10. The ventricular assist device of claim 9, wherein the one or more rechargeable batteries are recharged by external radio frequency waves or magnetic fields generated by one or more transmitting wire coils.

11. The ventricular assist device of claim 10, wherein the one or more transmitting wire coils are contained within a wearable device.

\* \* \* \* \*